United States Patent
Wang et al.

(10) Patent No.: US 9,236,622 B2
(45) Date of Patent: Jan. 12, 2016

(54) FUEL CELL SYSTEM WITH WETNESS SENSOR

(75) Inventors: Tie Wang, Rochester Hills, MI (US); Chendong Huang, Ann Arbor, MI (US); James A. Adams, Ann Arbor, MI (US); Shinichi Hirano, West Bloomfield, MI (US); George S. Saloka, Dearborn, MI (US); Mark S. Sulek, Sterling Heights, MI (US); James Waldecker, Farmington Hills, MI (US); Alireza Pezhman Shirvanian, Ann Arbor, MI (US)

(73) Assignee: Ford Global Technologies, LLC, Dearborn, MI (US)

(*) Notice: Subject to any disclaimer, the term of this patent is extended or adjusted under 35 U.S.C. 154(b) by 1007 days.

(21) Appl. No.: 12/537,483

(22) Filed: Aug. 7, 2009

(65) Prior Publication Data
US 2011/0033764 A1 Feb. 10, 2011

(51) Int. Cl.
*G01N 27/12* (2006.01)
*H01M 8/04* (2006.01)

(52) U.S. Cl.
CPC ......... *H01M 8/04253* (2013.01); *G01N 27/121* (2013.01); *H01M 8/045* (2013.01); *H01M 8/04507* (2013.01); *Y02E 60/50* (2013.01)

(58) Field of Classification Search
CPC .................................................. G01N 27/121
USPC ......................................... 73/335.02, 335.04
See application file for complete search history.

(56) References Cited

U.S. PATENT DOCUMENTS

| | | | |
|---|---|---|---|
| 4,050,048 A | 9/1977 | Frazee | |
| 4,280,115 A | 7/1981 | Farrington | |
| 4,422,129 A | 12/1983 | Briant et al. | |
| 4,707,244 A | 11/1987 | Harman, III et al. | |
| 4,975,249 A | 12/1990 | Elliott | |
| 5,045,828 A | 9/1991 | Kulwicki et al. | |
| 5,082,588 A | 1/1992 | Elliott | |
| 5,131,990 A | 7/1992 | Kulwicki et al. | |
| 5,364,185 A | 11/1994 | VanZandt et al. | |
| 5,393,404 A | 2/1995 | Greenblatt et al. | |
| 5,682,788 A | 11/1997 | Netzer | |
| 5,871,633 A | 2/1999 | Greenblatt et al. | |
| 6,020,744 A | 2/2000 | Ghorashi et al. | |

(Continued)

FOREIGN PATENT DOCUMENTS

| | | |
|---|---|---|
| EP | 9923482 B1 | 6/2003 |
| GB | 1113900 | 5/1968 |
| GB | 1464605 | 2/1977 |
| GB | 1482584 | 8/1977 |

OTHER PUBLICATIONS

Lee et al., Fabrication of Micro Sensors on a flexible substrate, May 13, 2008, Elsevier.*

(Continued)

*Primary Examiner* — Ula C Ruddock
*Assistant Examiner* — Frank Chernow
(74) *Attorney, Agent, or Firm* — Damian Porcari; Brooks Kushman P.C.

(57) ABSTRACT

A fuel cell system may have at least one sensor including a pair of electrodes disposed on a substrate. The sensor may be configured to produce an output signal having a magnitude that is proportional to a relative humidity in a vicinity of the sensor and, if liquid water is on the sensor, proportional to an amount of the liquid water on the sensor.

17 Claims, 2 Drawing Sheets

(56) References Cited

U.S. PATENT DOCUMENTS

| | | |
|---|---|---|
| 6,191,593 B1 | 2/2001 | Tartagni et al. |
| 6,690,569 B1 | 2/2004 | Mayer et al. |
| 6,742,387 B2 | 6/2004 | Hamamoto et al. |
| 6,796,166 B1 * | 9/2004 | Fountains et al. ............ 73/29.05 |
| 2002/0005068 A1 | 1/2002 | Libbrecht |
| 2003/0010119 A1 | 1/2003 | Toyoda |
| 2005/0112430 A1 | 5/2005 | Nuttall et al. |
| 2006/0121322 A1 | 6/2006 | Haas et al. |
| 2007/0003804 A1 | 1/2007 | Ogawa |
| 2007/0131020 A1 * | 6/2007 | Itakura et al. ................ 73/29.02 |

OTHER PUBLICATIONS

Crotzer et al. Sensors—Multifunctional Sensors: A new concept, May 1998.*

Sereda et al., Measurement of the Time-of-Wetness by Moisture Sensors and Their Calibration, 1982, p. 267-285.*

William Winn, An Electrostatic Theory for Instruments which measure the Radii of Water Drops by Detecting a Change in Capacity due to the Presence of a Drop, Journal of Applied Meteorology, Oct. 1968, p. 929-937.*

\* cited by examiner

US 9,236,622 B2

FUEL CELL SYSTEM WITH WETNESS SENSOR

BACKGROUND

A fuel cell is an electrochemical conversion device that produces electricity from a fuel and oxidant that react in the presence of an electrolyte. A single fuel cell may include a membrane electrode assembly and two flow field plates. Single cells may be combined into a fuel cell stack to produce the desired level of electrical power.

A fuel cell may include two electrodes, an anode and cathode, separated by a polymer membrane electrolyte. Each of the electrodes may be coated on one side with a thin platinum catalyst layer. The electrodes, catalyst and membrane together form the membrane electrode assembly.

Gases (hydrogen and air) may be supplied to the electrodes on either side of the membrane through channels formed in the flow field plates. Hydrogen flows through the channels to the anode. On the opposite side of the membrane, air flows through the channels to the cathode.

The hydrogen dissociates into free electrons and protons (positive hydrogen ions) in the presence of the platinum catalyst at the anode. The free electrons are conducted in the form of usable electric current through an external circuit. The protons migrate through the membrane electrolyte to the cathode. At the cathode, oxygen from the air, electrons from the external circuit, and protons combine to form water and heat.

SUMMARY

A fuel cell system may have at least one sensor including a pair of electrodes disposed on a substrate. The sensor may be configured to produce an output signal having a magnitude that is proportional to a relative humidity in a vicinity of the sensor and, if liquid water is on the sensor, proportional to an amount of the liquid water on the sensor.

The magnitude of the output signal may be based on an electrical potential difference between the electrodes.

The electrodes may be interdigitated.

One of the electrodes may be comprised of gold and the other of the electrodes may be comprised of copper.

The substrate may be comprised of FR4-laminate.

A fuel cell system may include a fuel cell stack, an air supply line in fluid communication with the fuel cell stack, a fuel supply line in fluid communication with the fuel cell stack, and a sensor disposed in one of the supply lines or the fuel cell stack. The sensor may include a pair of electrodes disposed on a substrate and configured to produce an output signal having a magnitude that is (i) proportional to a relative humidity in a vicinity of the sensor and (ii), if liquid water is on the sensor, proportional to an amount of the liquid water on the sensor.

A fuel cell system including at least one sensor having a pair of electrodes disposed on a substrate, the at least one sensor configured to produce an output signal having a magnitude that is proportional to an amount of liquid water on the sensor based on an electrical potential difference between the electrodes.

The substrate may be comprised of poly-oxydiphenylene-pyromellitimide.

While example embodiments in accordance with the invention are illustrated and disclosed, such disclosure should not be construed to limit the invention. It is anticipated that various modifications and alternative designs may be made without departing from the scope of the invention.

DETAILED DESCRIPTION

Figure 1:
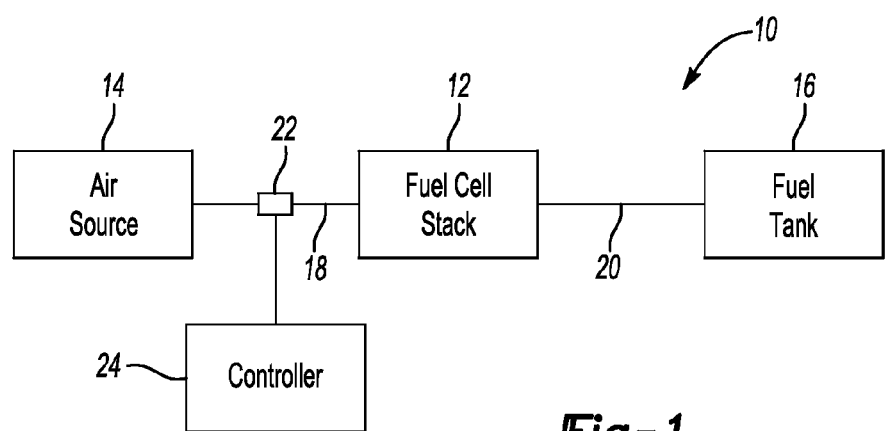
FIG. 1 is a block diagram of an embodiment of a fuel cell system.

Referring now to FIG. 1, an embodiment of a fuel cell system 10 may include a fuel cell stack 12, fuel tank 14, and air/oxygen source (e.g., ambient air) 16. The system 10 may also include an air conduit 18 and fuel conduit 20. The conduits 18, 20 direct fuel (e.g., hydrogen) and air, respectively, to the fuel cell stack 12 for consumption. Humidifiers, blowers, etc., may be positioned in/along the air conduit 18 as known in the art. Likewise, pumps, etc., may be positioned in/along the fuel conduit 20 as also known in the art.

In the embodiment of FIG. 1, the fuel cell system 10 is contained within an automotive vehicle. In other embodiments, the fuel cell system 10 may be a stand alone unit. Other configurations are also possible.

The fuel cell system 10 may further include a sensor 22 and a controller 24 in communication with the sensor 22. As explained below, the sensor 22 may be configured to detect an amount of liquid water on the sensor 22; the sensor 22 may also be configured to detect a relative humidity in the vicinity of the sensor 22.

In the embodiment of FIG. 1, the sensor 22 is disposed within the air conduit 18. Of course, multiple sensors 22 may be disposed throughout the fuel cell system 10. For example, sensors 22 (of differing configurations as detailed below) may be disposed within the fuel cell stack 12, within the fuel conduit 20, etc.

Water vapor and/or liquid water present in the fuel cell system 10 at shutdown may freeze (in cold conditions) and inhibit subsequent use. As known in the art, operating strategies (such as purging with dry air) to reduce/eliminate this water vapor and/or liquid water may be employed prior to shutdown.

Certain conventional operating strategies use ambient temperature as a proxy parameter to estimate the amount of water vapor and/or liquid water in the fuel cell system 10. This proxy parameter, for a variety of reasons, may be inaccurate. These inaccuracies may lead to undesirable circumstances. If, for example, there is less water vapor and/or liquid water in the fuel cell system 10 than estimated by the proxy parameter, the fuel cell system 10 may experience over-drying (and consume more power than necessary). If, for example, there is more water vapor and/or liquid water in the fuel cell system 10 than estimated by the proxy parameter, the fuel cell system 10 may experience under-drying (and thus subsequent freezing).

Figure 2:
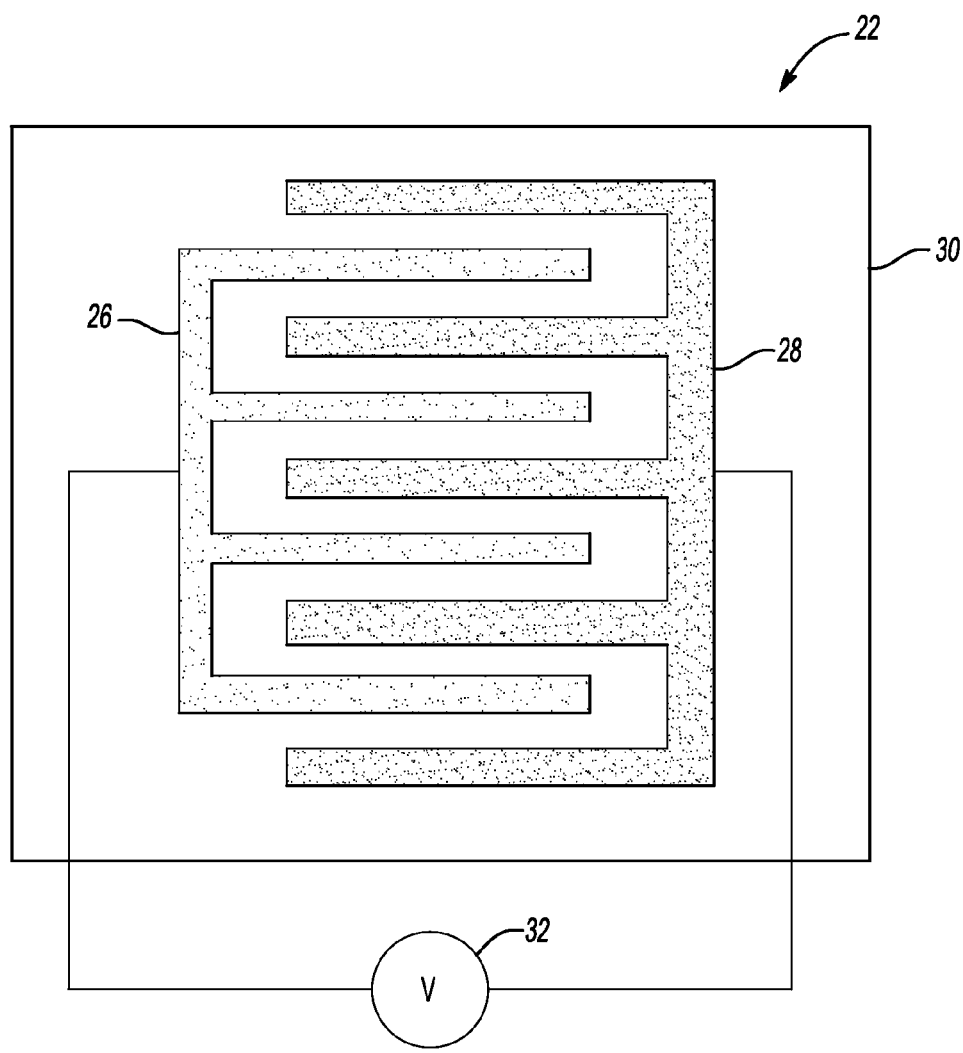
FIG. 2 is a schematic diagram of an embodiment of the sensor of FIG. 1.

Referring now to FIG. 2, an embodiment of the sensor 22 includes a pair of electrodes 26, 28 deposited on a substrate 30. In the embodiment of FIG. 2, the electrodes 26, 28 are gold and copper respectively, and interdigitated. In other embodiments, the electrodes 26, 28 may take any suitable form, e.g., noninterdigitated, serpentine, etc., and be made from any suitable material, e.g., various other metals, etc. The substrate 30 may be made from poly-oxydiphenylene-pyromellitimide (KAPTON by DuPont) or FR4-laminate. Other suitable substrate materials, however, may be used.

The sensor 22 may also include a volt-meter 32. If water vapor or liquid water, for example, is present on the surface of the sensor 22, a galvanic potential develops across the electrodes 26, 28. This potential can be measured by the voltmeter 32. As discussed below, this potential may indicate the relative humidity (if water vapor is on the surface of the sensor 22) and/or amount of liquid water (if liquid water is on the surface of the sensor 22) in the vicinity of the sensor 22.

Figure 3:
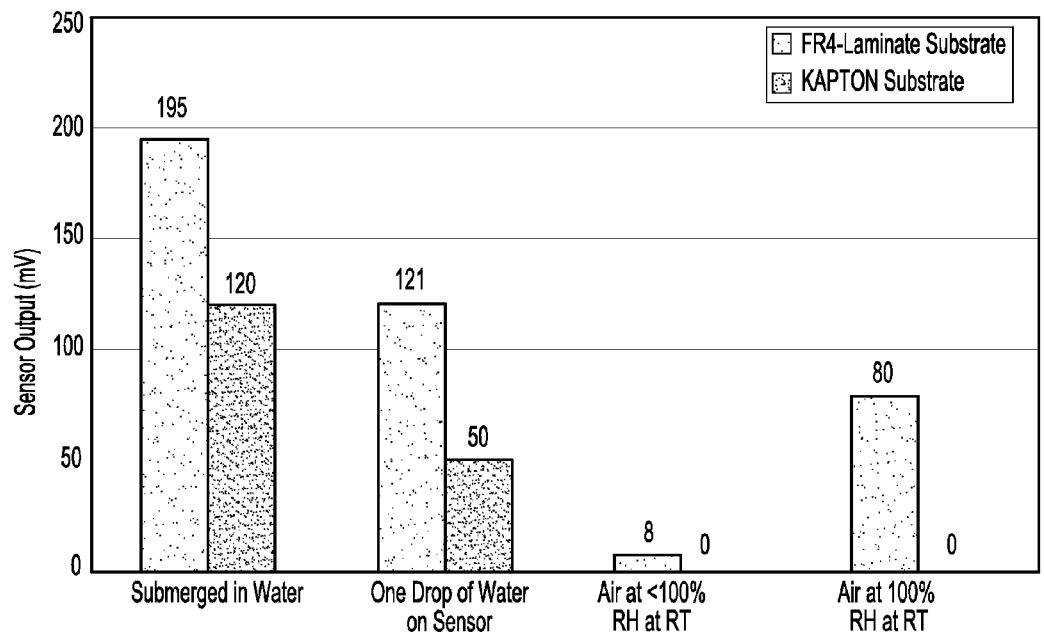
FIG. 3 is a bar chart illustrating example experimental results associated with two different sensor configurations.

Referring now to FIG. 3, experimental tests were performed on two sensors having different configurations. The first sensor included gold and copper interdigitated electrodes deposited on FR4-laminate. The second sensor included gold and copper interdigitated electrodes deposited on KAPTON. (The sensors only differed in their substrate material.)

Each of the sensors was (1) submerged in water, (2) had a drop of water placed on them, (3) exposed to room temperature air at a relative humidity of less than 100%, and (4) exposed to room temperature air at a relative humidity of 100%. The potential (in millivolts) between the electrodes was measured for each sensor under each of the above conditions.

The data of FIG. 3 reveals that the sensor having the KAPTON substrate produces an output signal proportional to the amount of water on the sensor. The data of FIG. 3 also reveals that the sensor having the FR4-laminate substrate produces an output signal proportional to the relative humidity in the vicinity of the sensor, and proportional to the amount of water on the sensor.

The sensor having the KAPTON substrate produced (1) no sensor output when exposed to room temperature air at less than 100% relative humidity, (2) no sensor output when exposed to room temperature air at 100% relative humidity, (3) a 50 millivolt sensor output when a drop of water was placed on the sensor, and (4) a 120 millivolt sensor output when submerged in water. This sensor (once calibrated) may thus be used to not only measure whether there is liquid water in the vicinity of the sensor but also the amount of liquid water in the vicinity of the sensor.

The sensor having the FR4-laminate substrate produced (1) an 8 millivolt sensor output when exposed to room temperature air at less than 100% relative humidity, (2) an 80 millivolt sensor output when exposed to room temperature air at 100% relative humidity, (3) a 121 millivolt sensor output when a drop of water was placed on the sensor, and (4) a 195 millivolt sensor output when submerged in water. This sensor (once calibrated) may thus be used as both a liquid water and relative humidity sensor.

Figure 4:
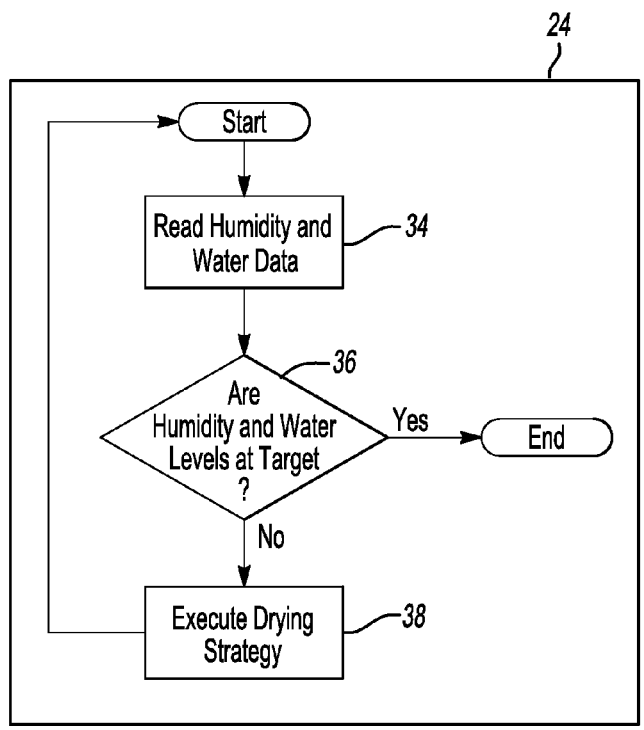
FIG. 4 is a flow chart illustrating a strategy for drying the fuel cell system of FIG. 1 prior to shut-down.

Referring now to FIGS. 1 and 4, relative humidity and water data collected by the sensor 22 (having, for example, gold and copper electrodes deposited on an FR4-laminate substrate) may be used as an input to a (closed-loop) control strategy governed by the controller 24 to efficiently dry the fuel cell system 10. As indicated at 34, the controller 24 reads the humidity and water data from the sensor 22. As indicated at 36, the controller 24 determines whether the humidity and water levels are at or below target levels. If yes, the strategy ends. If no, the controller 24 executes a drying strategy (e.g., purging with dry air) for a specified period of time as indicated at 38. The strategy then returns to 34.

The strategy discussed with reference to FIG. 4 may minimize the amount of energy used to reduce/eliminate water vapor and/or liquid water in the fuel cell stack 12 and the air conduit 18 because the strategy provides closed-loop feedback regarding the humidity and water levels. The strategy with reference to FIG. 4 may also avoid under-drying and/or over-drying the fuel cell stack 12 for the same reasons.

While embodiments of the invention have been illustrated and described, it is not intended that these embodiments illustrate and describe all possible forms of the invention. The words used in the specification are words of description rather than limitation, and it is understood that various changes may be made without departing from the spirit and scope of the invention.

What is claimed:

1. A fuel cell system comprising:
   at least one sensor including a pair of electrodes disposed on a substrate, the sensor being calibrated to produce an output signal having a magnitude that is (i) proportional to a relative humidity in a vicinity of the sensor during a first instance while exposed to water vapor and (ii), proportional to an amount of liquid water on the sensor during a second instance while exposed to liquid water.

2. The system of claim 1 wherein the magnitude of the output signal is based on an electrical potential difference between the electrodes.

3. The system of claim 1 wherein the electrodes are interdigitated.

4. The system of claim 1 wherein the electrodes are metallic.

5. The system of claim 4 wherein one of the electrodes is comprised of gold and the other of the electrodes is comprised of copper.

6. The system of claim 1 wherein the substrate is comprised of FR4-laminate.

7. A fuel cell system comprising:
   a fuel cell stack;
   an air supply line in fluid communication with the fuel cell stack;
   a fuel supply line in fluid communication with the fuel cell stack; and
   a sensor disposed in one of the supply lines or the fuel cell stack, the sensor including a pair of electrodes disposed on a substrate and calibrated to produce an output signal having a magnitude that is (i) proportional to a relative humidity in a vicinity of the sensor during a first instance while exposed to water vapor and (ii) proportional to an amount of liquid water on the sensor during a second instance while exposed to liquid water.

8. The system of claim 7 wherein the magnitude of the output signal is based on an electrical potential difference between the electrodes.

9. The system of claim 7 wherein the electrodes are interdigitated.

10. The system of claim 7 wherein the electrodes are metallic.

11. The system of claim 10 wherein one of the electrodes is comprised of gold and the other of the electrodes is comprised of copper.

12. The system of claim 7 wherein the substrate is comprised of FR4-laminate.

13. A fuel cell system comprising:
    at least one sensor having a pair of electrodes disposed on a substrate, the at least one sensor being calibrated to produce an output signal having a magnitude that is proportional to an amount of liquid water on the sensor based on an electrical potential difference between the electrodes.

14. The system of claim 13 wherein the electrodes are interdigitated.

15. The system of claim 13 wherein the electrodes are metallic.

16. The system of claim 15 wherein one of the electrodes is comprised of gold and the other of the electrodes is comprised of copper.

17. The system of claim 13 wherein the substrate is comprised of poly-oxydiphenylene-pyromellitimide.

* * * * *